(12) United States Patent
Rheinberger et al.

(10) Patent No.: US 6,287,490 B2
(45) Date of Patent: *Sep. 11, 2001

(54) METHOD FOR MANUFACTURING A DENTAL PROSTHESIS

(75) Inventors: Volker Rheinberger, Vaduz; Gerhard Zanghellini, Schaan, both of (LI)

(73) Assignee: Ivoclar AG (LI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/062,086

(22) Filed: Apr. 17, 1998

Related U.S. Application Data

(60) Provisional application No. 60/044,649, filed on Apr. 18, 1997.

(51) Int. Cl.[7] ............... A61C 13/003; A61C 13/087; A61C 13/20; A61C 13/34; A61C 13/00
(52) U.S. Cl. ............. 264/17; 264/16; 264/19; 264/222; 264/257; 264/313; 264/496; 264/101; 425/389; 425/405.1; 249/54; 433/215
(58) Field of Search ............... 264/16, 17, 19, 264/101, 220, 222, 257, 313, 496, 161; 106/35; 249/54; 433/215; 425/389, 405.1, 405.2, 806

(56) References Cited

U.S. PATENT DOCUMENTS

| | | | |
|---|---|---|---|
| 4,439,380 | * 3/1984 | Michl et al. | 264/16 |
| 4,894,012 | 1/1990 | Goldberg et al. | 433/215 |
| 5,023,041 | 6/1991 | Jones et al. | 264/510 |
| 5,098,304 | 3/1992 | Scharf | 433/215 |
| 5,104,591 | * 4/1992 | Masuhara et al. | 264/16 |
| 5,176,951 | 1/1993 | Rudo | 428/229 |
| 5,192,207 | * 3/1993 | Rosellini | 433/223 |
| 5,318,440 | * 6/1994 | Adam et al. | 433/8 |
| 5,324,186 | * 6/1994 | Bakanowski | 425/116 |
| 5,368,481 | 11/1994 | Hill | 433/159 |
| 5,698,020 | * 12/1997 | Salz et al. | 106/35 |
| 5,819,394 | * 10/1998 | Curtin | 29/527.2 |
| 5,839,900 | * 11/1998 | Billet et al. | 433/218 |
| 5,936,006 | * 8/1999 | Rheinberger et al. | 523/116 |
| 6,114,409 | * 9/2000 | Krebber | 523/116 |

FOREIGN PATENT DOCUMENTS

| | | | |
|---|---|---|---|
| 44 00 073 A1 | 7/1995 | (DE) | A61L/27/00 |
| 0 262 488 A1 | 4/1988 | (EP) | C08F/2/44 |
| 0 475 239 A2 | 3/1992 | (EP) | A61K/6/083 |
| 0 575 960 A1 | 12/1993 | (EP) | A61C/7/00 |
| 0 626 165 A1 | 11/1994 | (EP) | A61K/6/06 |
| 0 742 001 A2 | 11/1996 | (EP) | A61K/6/083 |
| 01078825 | 3/1989 | (JP) . | |
| WO 89/04640 | 6/1989 | (WO) . | |
| WO 95/08300 | 3/1995 | (WO) . | |

* cited by examiner

Primary Examiner—Jill L. Heitbrink
Assistant Examiner—Michael I. Poe
(74) Attorney, Agent, or Firm—Nixon Peabody LLP

(57) ABSTRACT

A method for manufacturing a fiber rein-forced composite dental restoration comprising the steps of (i) preparing a mould; (ii) filling the cavity of the mould with a fiber-reinforced polymerizable material comprising an organic matrix and a fiber component embedded within the matrix; (iii) applying pressure to the fiber-reinforced polymerizable material; and (iv) curing the fiber-reinforced polymerizable material. The method is characterized in that the mould is designed in a way which allows excess organic matrix material to escape form the cavity during pressing.

19 Claims, 7 Drawing Sheets

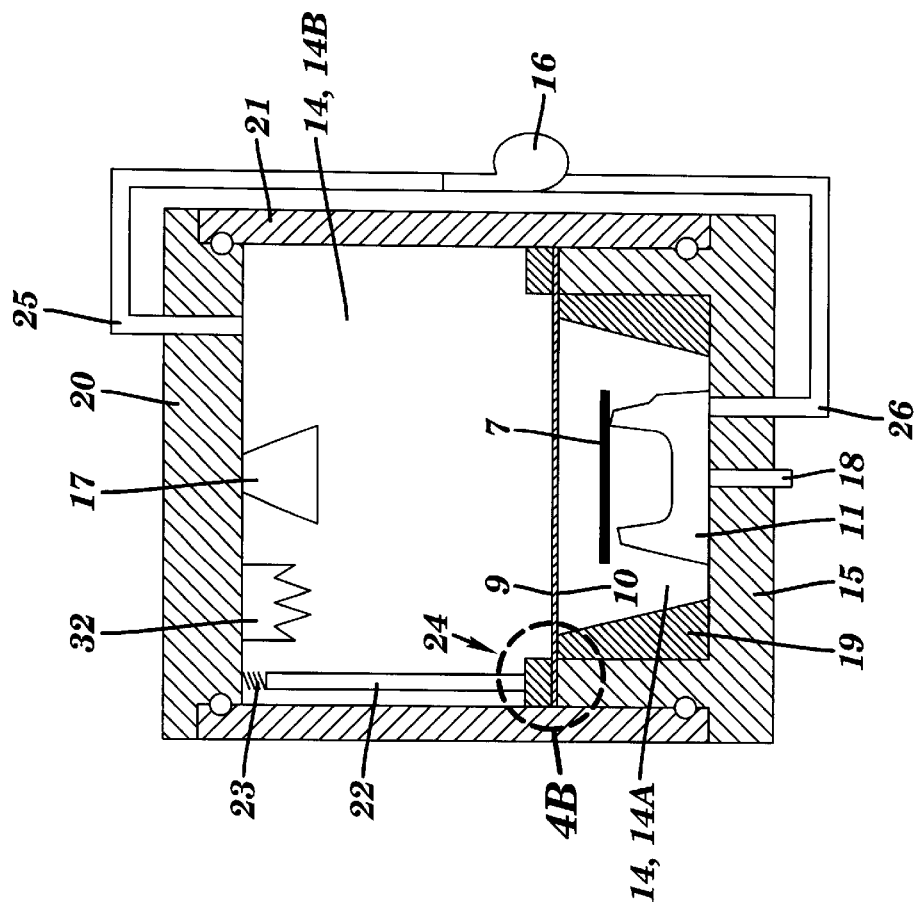
FIG. 4A
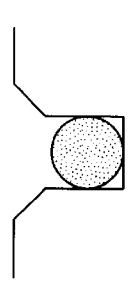
FIG. 3A
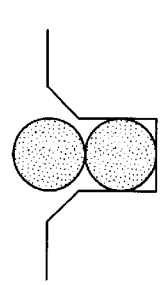
FIG. 3B
FIG. 3C
FIG. 3D
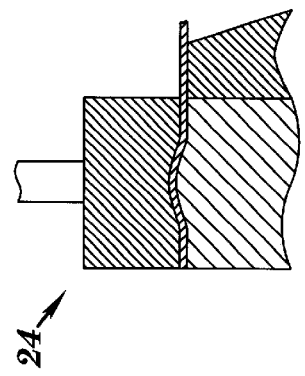
FIG. 4B GRAPH 1: THE VOLUME FRACTION OF FIBERS CAN BE CALCULATED USING THE LOSS OF IGNITION

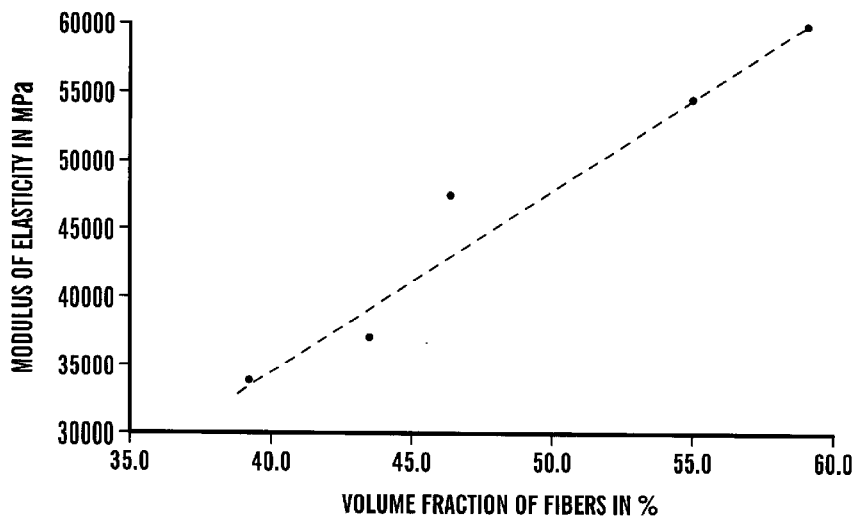
FIG. 9
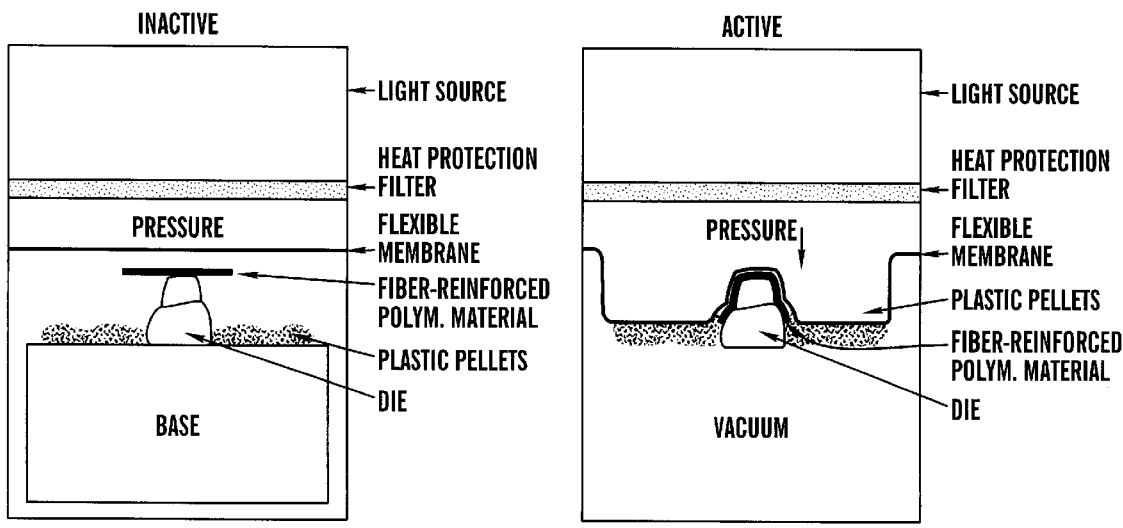
FIG. 10A  FIG. 10B

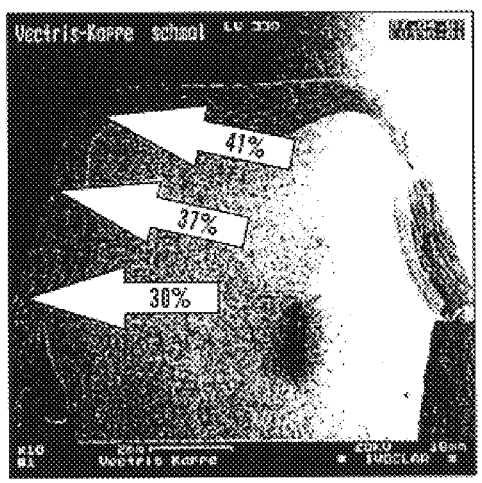
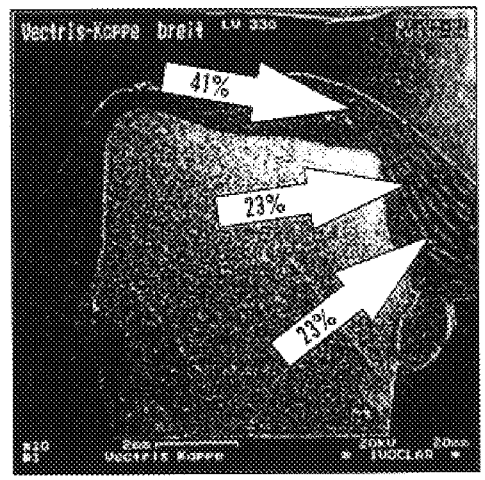
*FIG. 12*  *FIG. 13*

METHOD FOR MANUFACTURING A DENTAL PROSTHESIS

The present application claims priority benefit of U.S. patent application Ser. No. 60/044,649, filed Apr. 18, 1997, which is hereby incorporated by reference.

FIELD OF THE INVENTION

The invention relates to a method for manufacturing a fiber-reinforced composite especially a dental prosthesis such as a crown, bridge, implant superstructure, inlay bridge or removable dentures.

BACKGROUND OF THE INVENTION

U.S. Pat. No. 4,894,012 and WO 89/04640 disclose a two-step procedure for producing fiber-reinforced dental appliances. First, a fiber-reinforced composite material is produced having the requisite stiffness and strength characteristics and thereafter a dental device is formed therefrom. The composite material comprises essentially a polymeric matrix and a fiber component embedded within the matrix. The materials employed are preferably fully polymerized thermoplastic materials. Restorations such as bridges are prepared by heating the fiber-reinforced composite material with a heat gun until soft and then forming the material using a dental cast. Finally, acrylic teeth are fixed thereto.

U.S. Pat. No. 5,098,304 discloses a method for reinforcing composite resin systems for restoring or splinting teeth which utilizes glass fiber material. Bridges are formed by first preparing the teeth which are adjacent to the missing tooth by grinding and then fixing a mesh or rope of fiber glass to the teeth. Thereafter a replacement tooth is formed on the fiber glass material.

U.S. Pat. No. 5,176,951 and WO 91/11153 disclose a method of reinforcing a resin portion of a dental structure, which comprises the steps of applying one or more layers of a light weight woven fabric made up of polyaramide or polyethylene fibers to a resin portion of a dental structure and covering the woven fabric with more of the resin. In this method the fiber material and the resin have to be combined by the user when preparing the dental restoration. This is inconvenient and bears the risk of forming air pockets which cause destabilization of the restoration.

WO 95/08300 relates to a method for manufacturing a dental prostheses wherein a preimpregnated fabric part is placed on a shaping model and formed on the model by compression. Then the organic matrix of the preimpregnated fabric part is cross-linked to obtain a rigid support shell and successive layers of organic resin are applied onto the support shell to form an external finishing coating. The support shell comprises between 20 to 60% by volume of fibers and other inorganic charges.

For producing fiber-reinforced bridges it is known to first prepare a dental cast which is partially covered with silicon to form a mould leaving a cavity for the restoration to be made. Then a preimpregnated fabric part is placed in the cavity, formed according to the model by compression and hardened. This process allows for the convenient preparation of metal free dental prostheses. However, the use of preimpregnated fabric parts with a high fiber content requires high pressure during compressing. In contrast, use of preimpregnated fabric parts with a low fiber content result in restorations with a limited stability.

SUMMARY OF THE INVENTION

It is the object of the present invention to provide an improved method for manufacturing fiber reinforced composites with high fiber content from fabric parts or fiber material preimpregnated with an organic matrix which process does not require high pressure for forming the fiber reinforced material.

BRIEF DESCRIPTION OF THE DRAWINGS

FIG. 3 illustrates a third embodiment of the present invention.

FIG. 4 illustrates a machine used in the present invention.

FIG. 9 illustrates the relationship between modules of elasticity and the volume fraction of fibers for a material.

FIG. 10 illustrates a die in an embodiment of the machine shown in FIG. 4 before and after pressure is applied to the flexible membrane.

FIG. 12 is an electron microphotograph of a crown prepared with a die having a narrow shoulder.

FIG. 13 is an electron microphotograph of a crown prepared with a die having a wide shoulder.

This problem is solved by a method for manufacturing an fiber reinforced composite comprising the steps of (i) preparing a mould;

(ii) filling the cavity of the mould with a fiber-reinforced polymerizable material comprising an organic matrix and a fiber component embedded within the matrix;

(iii) applying pressure to the fiber reinforced polymerizable material; and (iv) curing the fiber-reinforced polymerizable material.

This method is characterized in that the mould is designed in a way which allows excess organic material to escape from the cavity during pressing.

In a preferred embodiment the mould is provided with one or more grooves connecting the inside of the cavity with the outside of the mould. The grooves are cut into the mould from top to the bottom and allow matrix monomer to flow out of the mould after pressure has been applied. Thus, the volume fraction of fibers is increased remarkably and the strength of the composite is increased.

Figure 1:
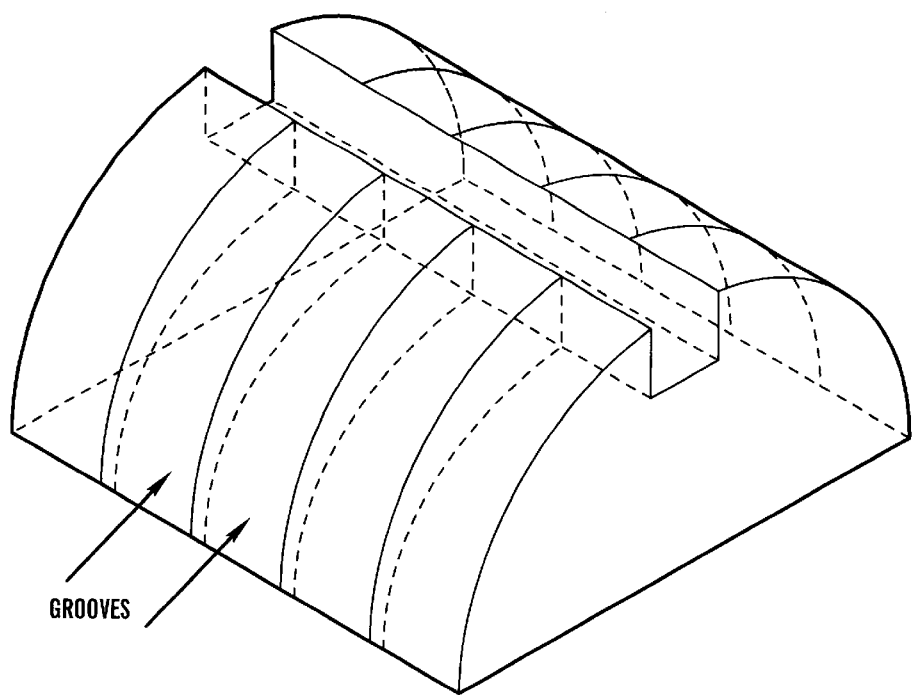
FIG. 1 shows a schematic view of one embodiment of a mould of the present invention.

A schematic view of a mould provided with a plurality of grooves is shown in FIG. 1. The grooves are preferably 0.05 to 1.5 mm wide, more preferably 0.05 to 1.0 mm, most preferably 0.2 to 1.0 mm.

Figure 2:
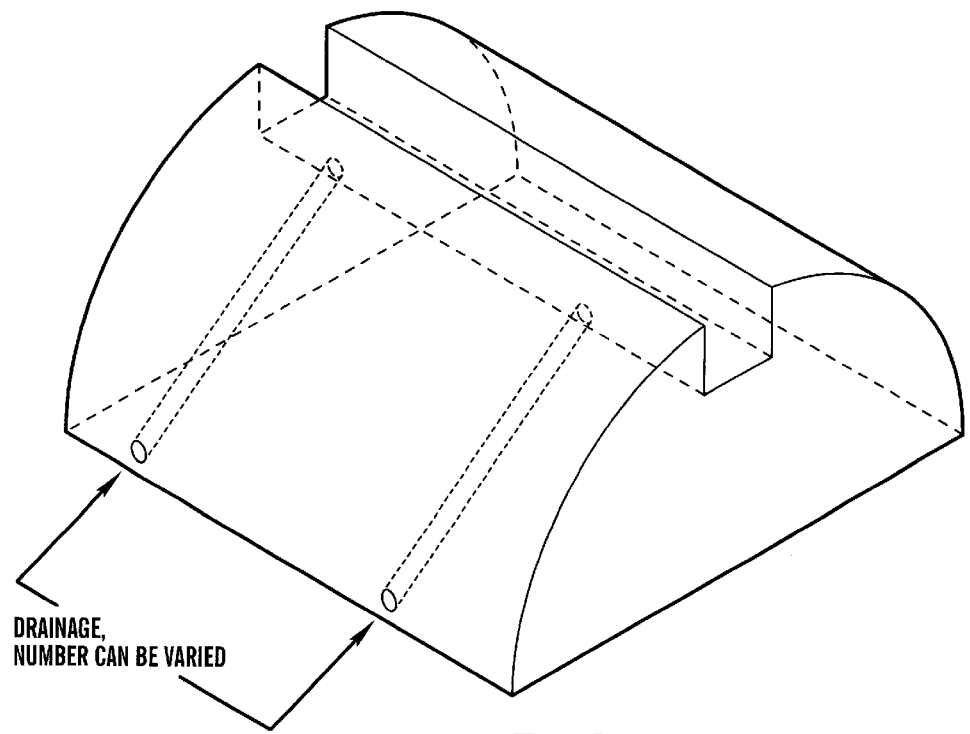
FIG. 2 illustrates a second embodiment of a mould of the present invention.

Another way to increase the volume fraction of fibers is to form one or more drainages. A schematic view of a mould provided with two drainages is shown in FIG. 2. The drainages preferably have a inner diameter of from 0.05 to 1.5 mm, more preferably 0.05 to 1.0 mm, most preferably 0.2 to 1.0 mm.

DETAILED DESCRIPTION OF THE INVENTION

The grooves and/or drainages should be applied on both sides of the cavity. The number of grooves and drainages depends on the size of the cavity. Moulds for the preparation of a dental bridge are usually provided with 2 to 4 grooves and/or drainages on each side of the mould, preferably 1 groove or drainage every 5 mm, more preferably 1 groove or drainage every 3 mm.

Still a further way to increase the volume fraction of fibers is to provide the mould with void space able to take up excess matrix material. A preferred way of providing void space is to make a bevelled cavity as is schematically shown in FIG. 3.

To ensure a high fiber content of the fiber-reinforced composite it is preferred to overfill the cavity of the mould with fiber-reinforced polymerizable material as is indicated in FIG. 3. During pressing excess matrix monomer flows out of the cavity via the grooves or drainages or is collected in the void space whereas the fiber material remains in the mould. It is preferred to overfill the cavity of the mould by 1 to 10% by volume, more preferably 5 to 15%.

For pressure application it is preferred to use an elastic membrane as disclosed in U.S. Pat. No. 5,839,900 which is hereby incorporated by reference. Although pressure may be applied by hand it is preferred to use an automated process and a machine as described in U.S. Pat. No. 5,839,900 which is hereby incorporated by reference.

A suitable machine is schematically shown in FIG. 4. This machine comprises a sealed enclosure 14, a plate 15 receiving a shaping model 11 in the enclosure 14, a flexible fluid-proof membrane 9, notably air-tight, separating the enclosure 14 into two chambers 14a, 14b, means 16, 25, 26 for creating a lower fluid pressure in the chamber 14b, and means 17, 18, 19, 32 for cross-linking the parts 7 placed on the shaping model 11 in the chamber 14a. According to the invention, the cross-linking means 17, 18, 19 are preferably light-curing means comprising at least one light source 17 located in the chamber 14b opposite the one 14a containing the shaping model 11. The flexible separating membrane 9 is then translucent or transparent, i.e. it lets light pass. The cross-linking means 17, 18, 19 comprise at least one light conveying duct 18 giving out onto the receiving plate 15 to light from the inside the shaping model 11 itself made of translucent or transparent material. In this way, lighting from the inside is achieved and the efficiency of the cross-linking is improved. In addition, the cross-linking means 17, 18, 19 can comprise a peripheral mirror 19 surrounding the shaping model 11 to improve the light diffusion. Instead of, or in combination with the cross-linking means 17, 18, 19 the machine of the invention can comprise chemical and/or cross-linking means 32.

The enclosure 14 is formed by the lower plate 15 receiving the shaping model 11, a similar parallel upper plate 20 forming a cover, and a cylinder 21 placed between these two plates 15, 20 in a fluid-proof manner. The cylinder 21 can be transparent in order to visually monitor the execution of the manufacturing process. The upper plate 20 supports a plurality of small columns 22 with compression springs 23 located at regular intervals on its circumference and designed to press against the peripheral edge of the membrane 9 to wedge it against a cylindrical protuberance 24 of the lower plate 15. The small columns 22, springs 23 and protuberance 24 thus form removable securing means of the membrane 9 separating the two chambers 14a, 14b. The membrane can thus easily be changed as required each time the machine is disassembled, i.e. each time manufacture of a prosthesis is prepared. The lower plate 15 is rigidly associated, in a tight but disassembled manner, to the cylinder 21 in order to enable changing of the membrane 9 and/or preparation of the shaping model 11 and of the parts 7 to be polymerized. The light source 17 can be simply formed by an electrical light bulb. The pressure difference between the two chambers 14a, 14b can be achieved by inlet of a compressed fluid such as air or a liquid into the chamber 14b via the orifice and/or by suction of a fluid form the chamber 14a containing the shaping model 11 via a suction orifice 26. For example, the suction orifice 26 and the inlet orifice 25 can be connected to one another by means of fluid pump 16. Due to the effect of the pressure difference thus achieved, the flexible membrane 9 is pressed against the shaping model 11 and thus presses the pre-impregnated fabric part 7 against this shaping model 11. The lighting means 17, 18 are then switched on causing photopolymerisation of the organic matrix of the preimpregnated fabric part 7 and formation of the support shell 2. The membrane typically is formed by an elastic synthetic material such as a copolymer or rubber.

The method of the present invention allows the manufacturing and forming of fiber reinforced composites having a final fiber content of up to 60% by volume by use of a pressure of not more than 1.5 to 2.5 bar, preferably about 2 bar.

The fiber-reinforced composite may be further processed by application of one or more layers of an organic resin as disclosed in U.S. Pat. No. 5,839,900 which is hereby incorporated by reference, i.e. applying at least one layer of an organic resin to the composite and cross-linking the same.

The preparation of the mould is well known in the art (see for example K. H. Körber, Dentalspiegel Labor 3/96; J. Langner, Quintessenz Zahntechnik 23, 5, 1997, pages 631–646). Preferably a silicon material such as condensation or addition silicon is used for forming the mould.

The method of the present invention is especially suitable for producing fiber-reinforced composites such as dental prostheses, such as crowns, bridges, inlay bridges, implanted prostheses, implant superstructures, removable appliances, removable dentures or structural components of dental restorations such as a support shell.

A mould for, e.g. preparing a bridge or a structural component of a bridge is preferably prepared by
  (a) first preparing a cast of the tooth or teeth which is to be restored;
  (b) forming a wax model of the dental restoration on the dental cast;
  (c) applying a covering agent to the model and the cast to form the mould;
  (d) removing the wax model from the mould to leave a cavity for the restoration.

This process is comparable to the "lost-wax-technique" and well-known to the expert in the field.

The fiber-reinforced polymerizable material used for manufacturing the fiber-reinforced composites comprises an organic matrix and a fiber component embedded within the matrix.

For manufacturing dental restorations the fiber component is preferably a uniform mesh, a random mesh, or a rope or thread type material. The fibers may also take the form of long continuous filaments or may be woven in a leno weave as disclosed in U.S. Pat. No. 5,176,951 which is hereby incorporated by reference. Most preferably a fiber-meshed fabric is used. The fibers are preferably made from glass, ceramic, silica or organic materials such as aramid, polyethylene, carbon and boron. Fibers of ceramic, silica and especially glass are most preferred.

The fiber content of the fiber reinforced polymerizable material is preferably in the range of 7 to 94% by weight, more preferably 28 to 82% by weight and most preferably 45 to 65% by weight.

Preferred organic matrix monomers are methacrylate resins, especially dimethacrylate resins such as dimethacrylate-based aromatic resins, epoxy-based aromatic resins, polymethacrylate resins and mixtures thereof. The matrix can also comprise urethane methacrylate resins. Among the aromatic dimethacrylate resins, bisphenol-A-derivatives such as bisphenol-A-glycidyl-dimethacrylate (bis-GMA), urethane-methacrylate (UDMA), triethylene glycol dimethacrylate (TEDMA) and mixtures thereof are preferred.

According to the invention, a bis-GMA-base resin can be used modified by copolymerization with composites of lower molecular weight, notably as non-restrictive examples bisphenol glycidyl-dimethacrylates (BIS-MA), bisphenol ethyl-methacrylates (BIS-EMA), bisphenol propyl-methacrylates (BIS-PMA), ethylene glycol-dimethacrylates (EGDMA), diethylene glycol-dimethacrylates (DEGDMA), triethylene glycol-dimethacrylates (TEGDMA), triethy-lene glycol-methacrylates (TEGMA), methyl-methacrylates (MMA), and polyurethane fluor-methacrylates (PFUMA).

The fiber-reinforced polymerizable material preferably comprises 31.1 to 48.9% by weight of the organic matrix material. Preferably a mixture of Bis-GMA, decandiol dimethacrylate, triethyleneglycol dimethacrylate and urethane dimethacrylate is used, more preferably a mixture comprising 24.5 to 38.6% by weight Bis-GMA, 0.3 to 0.5% by weight decandiol dimethacrylate, 6.2 to 9.7% by weight triethyleneglycol dimethacrylate and 0.1% by weight urethane dimethacrylate. If not indicated otherwise all percentages refer to the total weight of the fiber-rein-forced polymerizable material.

The fiber reinforced polymerizable material may additionally comprise fillers and additives.

Suitable fillers are silica-base particles whose diameter can vary from 0.1 to 100 μm, for example pyrolytic silica, and/or glass or ceramic-base particles, notably glass or borosilicate particles, ceramic glasses, barium-aluminum particles and/or strontium-aluminum particles. Also, radio-opaque heavy metals can be incorporated, such as niobium, tin and/or titanium, or organic or mineral pigments. Preferred fillers are highly dispersed silica and glass or ceramic fillers with a medium particle size of $\leq 1.5$ μm.

The additional fillers are preferably used in an amount of 1 to 30 wt. %, more preferably 2 to 15 wt.% and most preferably 3.5 to 5.5% by weight. It is especially preferred to use 3.5 to 5.5% by weight of highly dispersed silica as addition filler. Other additives such as pigments are typically used ill an amount of less than 0.1% by weight.

The inorganic particles and fibers are treated before being incorporated in the organic matrix by means of organo-silano compounds such as aryloxy-silanes and/or halosilanes such as (meth)acryloyl-alkoxy-silanes.

The fiber reinforced polymerizable materials contain at least one polymerization initiator and optionally an accelerator and/or stabilizers. The materials can be hardened by heats light or microwave curing.

The known peroxides such as dibenzoylperoxide, dilauroylperoxide, tert-butylperoctoate or tert-butylperbenzoate can be used as initiators for hot polymerization. 2,2'-azobisisobutyronitril (AIBN), benzpinacol and 2,2'-dialkylbenzpinacols are also suiteable.

In a preferred embodiment the fiber reinforced polymerizable material contains a photoinitiator such as diketones, preferably diacetyl and/or quinones such as camphor quinone arid acenaphthene quinone. The photoinitiators may also be combined with an accelerator such as an amine.

The concentration of initiators and accelerators preferably lies in the range of 0.01 to 3.0 wt. %, particularly preferably in the range from 0.05 to 1.0 wt. %, relative to the quantity of monmers used in the dental material.

The total amount of catalysts and stabilizers is typically in the range of 0.3 to 0.5% by weight, based on the total composition.

For producing the fiber-reinforced composites the fiber-reinforced polymerizable materials are preferably used in form of a fabric part preimpregnated with an organic matrix. The fiber-reinforced polymerizable materials may be applied in successive layers which can be cured before applying the next layer. Fiber-reinforced polymerizable materials having different fiber contents may be combined for producing one fiber-reinforced composite. For preparing a dental bridge or a structural component of a bridge it is preferred to combine one or more preimpregnated fabric parts in form of a flat sheet or a disc and a joining element such as a bar like element.

Generally, the fiber reinforced polymerizable material can be of any shape such as a flat sheet, a disc, a bar, or a wire. Before placing the fiber-reinforced polymerizable material in the cavity of the mould the material may be cut according to necessity.

Table 1 shows the composition of preferred fiber-reinforced polymerizable materials according to the present invention, composition No. 2 being especially preferred.

The external finishing coating can be formed by a filled cosmetic resin, notably of the type formed by bis-phenol-A-derivatives such as bis-GMA and the other resins mentioned above, charged in such a way that it has a high rigidity, a great resistance to abrasion and a colour shade close to that of the natural tooth. Charged cosmetic resins of this kind are known as such.

TABLE 1

Compositions of most preferred fiber-reinforced polymerizable materials

| Composition | Composition No. 1 (% by weight) | Composition No. 2 (% by weight) | Composition No. 3 (% by weight) |
|---|---|---|---|
| Bis-GMA | 38.6 | 24.5 | 35.2 |
| Decandiol dimethacrylate | 0.5 | 0.3 | 0.4 |
| Triethyleneglycol dimethacrylate | 9.7 | 6.2 | 8.8 |
| Urethane dimethacrylate | 0.1 | 0.1 | 0.1 |
| High dispersed silica | 5.5 | 3.5 | 5.0 |
| Catalysts and Stabilizers | <0.5 | <0.3 | <0.4 |
| Pigments | <0.1 | <0.1 | <0.1 |
| Glass fibers | 45.0 | 65.0 | 50.0 |

It has been found that the fiber content of a fiber-reinforced composite could be increased for instance from 43.3 vol. % to 47.7 vol. % if the material is compressed in a mould according to the present invention using a pressure of about 2 bar (Table 2). This is an increase of the fiber content more than 10%. The increase of fiber content resulted in an increase of flexible strength and modulus of elasticity of about 15%.

Figure 5:
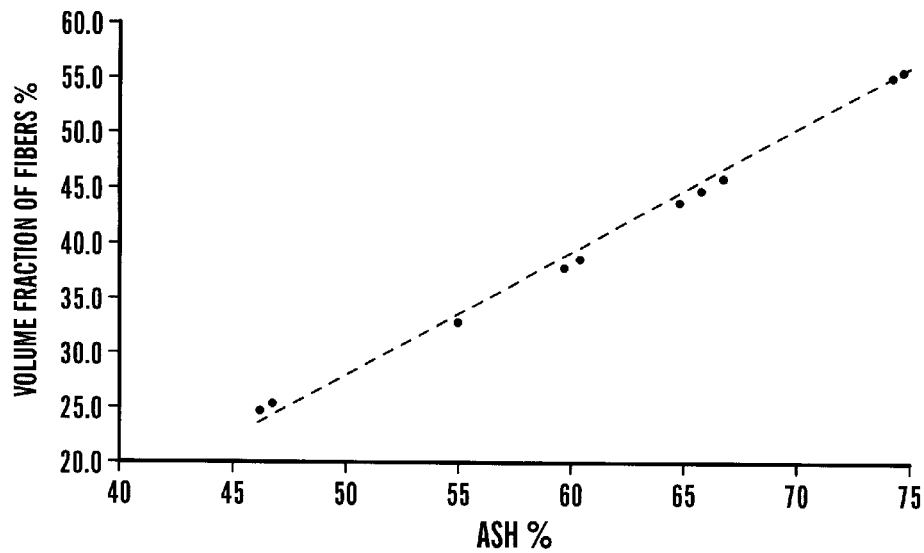
FIG. 5 illustrates the relationship between loss of ignition and the volume fraction of fibers for various compositions.

The fiber content of the fiber-reinforced composites comprising inorganic fibers is determined via loss of ignition (LOI). The organic matrix material of the fiber-reinforced composite is burned at 850° C. for 1.5 hours and the inorganic reminder (ash or loss of ignition, LOI) determined gravimetrically. The relation between LOI and the volume fraction of fibers for Compositions No. 1, No. 2 and No. 3 is shown in FIG. 5. As can be seen LOI and volume fraction of fibers are linearly correlated. By linar regression analysis the following equation can be derived from FIG. 5:

vol. %=1.064×LOI−23.4

The fiber content of fiber-reinforced composites comprising organic fibers can be determined by scanning electron mircroscopy.

Figure 6:
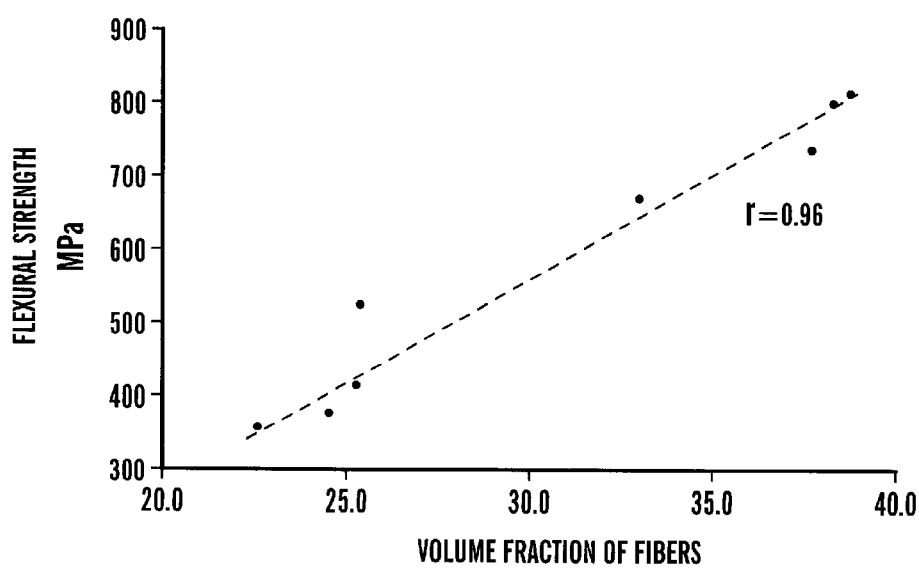
FIG. 6 illustrates the relationship between flexural strength and the volume fraction of fibers for a material.
Figure 7:
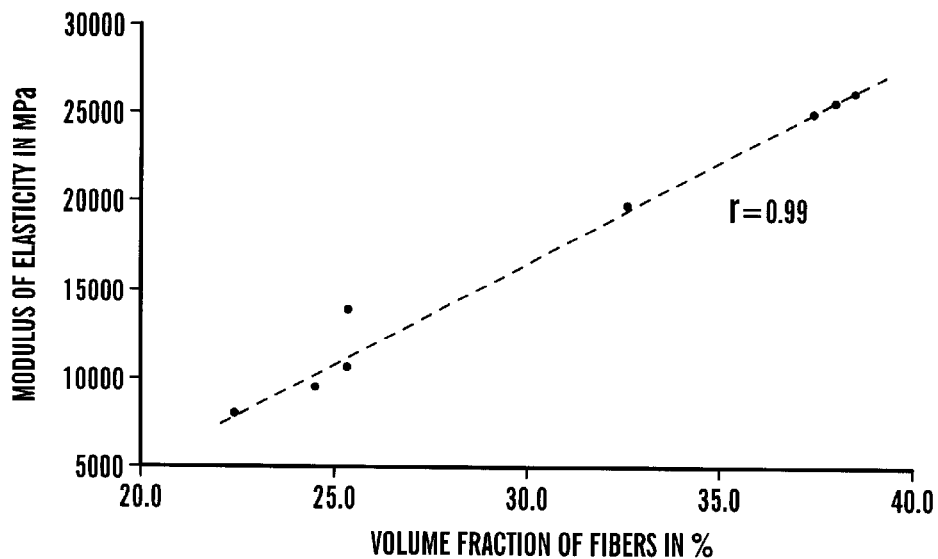
FIG. 7 illustrates the relationship between modules of elasticity and the volume fraction of fibers for a material.
Figure 8:
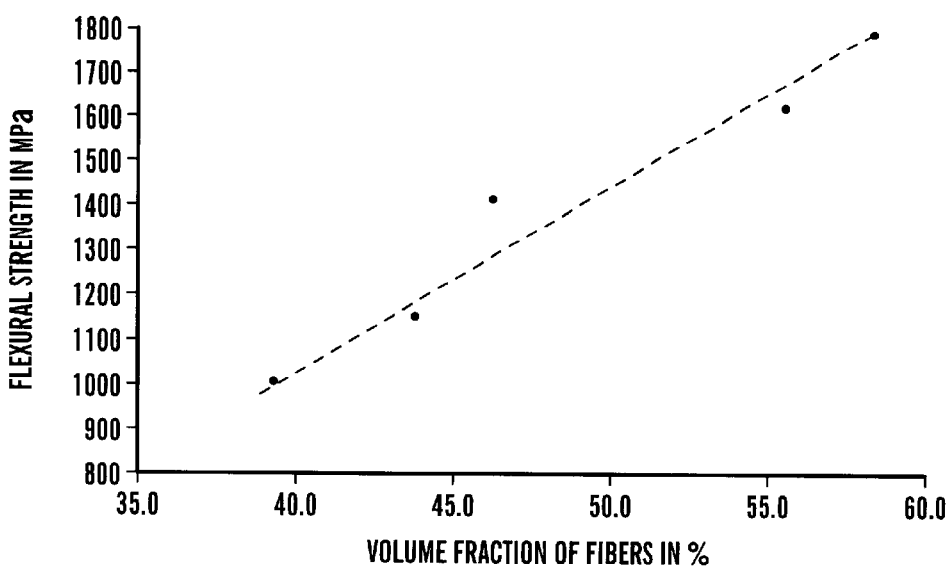
FIG. 8 illustrates the relationship between flexural strength and the volume fraction of fibers for a material.

It was further found that the modulus of elasticity and the flexural strength are linearly correlated to the volume fraction of fibers in percent. Thus, fiber-reinforced composites having the desired physical properties can be produced by adjusting the volume fraction of fibers to a suitable value. FIGS. 6 and 7 show the relationship between flexural strength and modulus of elasticity, respectively, and the volume fraction of fibers for the preferred material No. 1, and FIGS. 8 and 9 for the preferred material No. 2.

The fiber-reinforced composite obtained after the first curing step may be further improved by implying additional layers of fiber-reinforced polymerizable material. For this purpose the mould is preferably cut back to lay bare the dental cast and to form a die. Further layers of fiber-reinforced polymerizable material are placed on the die as shown schematically in FIG. 10. FIG. 10 shows a die placed in a machine as shown in FIG. 4. During pressure application the membrane presses the fiber-reinforced polymerizable material on the die. Hardening is achieved by photopolymerisation.

Figure 11A:
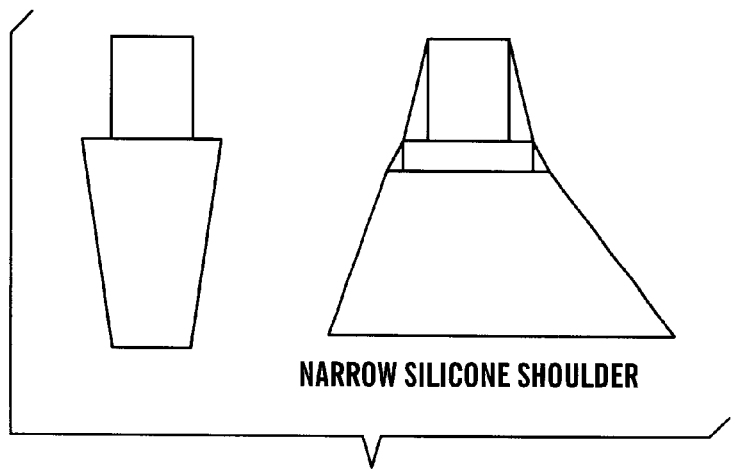
FIGS. 11A and 11B illustrate two schematic views of a die having a narrow shoulder (FIG. 11A) and a wide shoulder (FIG. 11B).
Figure 11B:
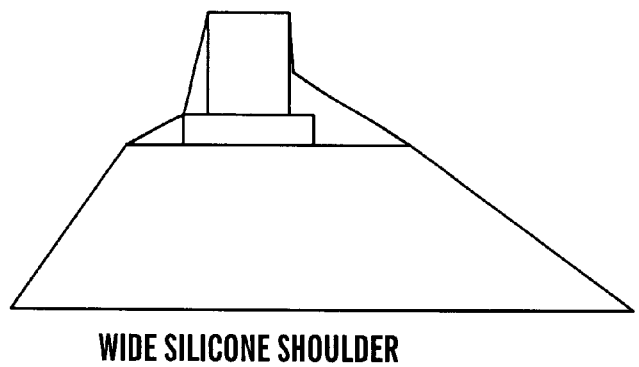

It was found that the fiber content of the additional layers is influenced by the form of the die. To increase the strength of the fiber-reinforced composite it is preferable to make a narrow shoulder as is schematically shown in FIG. 11, i.e. the shoulder follows the line of the wall of the tooth to be restored and steps are to be avoided. The term "narrow shoulder" refers to shoulders with steps preferably having an edge length of 0 to 1.0 mm, more preferably 0 to 0.5 mm.

For manufacturing e.g. a crown it is usually not necessary to prepare a mould. In this case the fiber-reinforced composite is prepared by (1) first preparing a cast of the tooth which is to be restored;

(2) applying a covering agent to the model and the cast to cover the cast and leaving only the tooth to be restored uncovered;

(3) placing a fiber-reinforced polymerizable material comprising an organic matrix and a fiber component embedded onto the uncovered tooth;

(4) applying pressure to the fiber-reinforced polymerizable material;

(5) curing the fiber-reinforced polymerizable material.

The shoulder of the die is preferably formed as discussed above.

FIG. 12 shows a picture of a electron microphotograph of fiber-reinforced composite prepared by use of a narrow shoulder and FIG. 13 of a fiber-reinforced composite prepared by use of a wide shoulder. The volume fraction of fibers was measured at three different sections of the fiber-reinforced composite by determining the LOI of different sections of the composite. In the composite produced by use of a narrow shoulder the fiber content ranges from 30 to 41% whereas in case of the wide shoulder a fiber content from 23 to 41% was found. The strength of the fiber-reinforced composites can be determined by use of the graphs of FIGS. 6 to 9.

EXAMPLES

In the following the present invention will be further illustrated by use examples.

Example 1

A silicon mould with a cavity of 3×3×36 mm was made. The cavity was filed with material No. 2 (see Table 1 above) and covered with an elastic membrane. The membrane was pressed onto the mould with a pressure of approximately 2 bar in a machine as shown in FIG. 4 (VECTRIS® VS1, Ivoclar). Two minutes after pressure application the light source was switched on and the material cured within 7 minutes. In a first test series the cavity of the mould was underfilled, in a second series overfilled. This procedure was repeated with moulds provided with a 3 grooves having a width of 1 mm or 2 drainages having a inner diameter of 1 mm on each side. In a further test bevelled and non-bevelled moulds were used. The flexural strength and the modulus of elasticity of the bodies prepared was tested according to ISO 10477. The results are shown in Table 2.

Table 2 shows that moulds with grooves and drainage tubes generally result in a higher fiber content. The highest strength and fiber volume was achieved with an overfilled mould with grooves. Bevelled moulds also resulted in an increase of fiber content and strength.

TABLE 2

Fiber content and mechanical properties of fiber reinforced composites

| | | mould without drainage | mould with grooves | mould with drainage tubes |
|---|---|---|---|---|
| under-filled not bevelled | ash | 61.2% | 61.8 % | 61.5% |
| | Vol. fraction in % | 41.7% v | 42.3% v | 42.2% v |
| | flexural strength | 1105 MPa | 1129 MPa | 1125 MPa |
| | modulus of elast. | 37140 MPa | 37936 MPa | 37804 MPa |
| over-filled not bevelled | ash | 62.7% | 66.8% | 65.1% |
| | Vol. fraction in % | 43.3% v | 47.7% v | 45.9% v |
| | flexural strength | 1170 MPa | 1347 MPa | 1275 MPa |
| | modulus of elast. | 39263 MPa | 45101 MPa | 42713 MPa |
| under-filled bevelled | ash | 61.6% | 63.5% | 63.8% |
| | Vol. fraction in % | 42.1% v | 44.1% v | 44.5% v |
| | flexural strength | 1121 MPa | 1202 MPa | 1218 MPa |
| | modulus of elast. | 37671 MPa | 40325 MPa | 40855 MPa |
| over-filled bevelled | ash | 60.6% | 64.9% | 62.8% |
| | Vol. fraction in % | 40.8% v | 45.4% v | 43.2% v |
| | flexural strength | 1068 MPa | 1254 MPa | 1165 MPa |
| | modulus of elast. | 35946 MPa | 42048 MPa | 39130 MPa |

Example 2

A dental cast was made from a tooth prepared for receiving a crown. The cast was covered with condensation silicon mass (Optosil®, Bayer) in a way that only the tooth stump to be restored remained uncovered. In the first test a narrow silicon shoulder was prepared and in the second test a wide shoulder. A disc shaped preimpregnated fabric part (Table 1, No. 1) was placed on the stump and shaped on the model by compression with a flexible membrane as shown in FIG. 10. The preimpregnated fabric part was light cured as described in Example 1. Then the fiber content at three different sections of the fiber-rein-forced composite was determined by cutting the composite into pieces and measuring the LOI (% ash). The strength at the three sections was estimated using the graphs of FIGS. 7 and 8. The results are shown in Table 3 and FIGS. 12 and 13.

TABLE 3

Fiber content and mechanical properties in different sections of fiber reinforced coposites

|  |  | Narrow silicone shoulder | wide silicone shoulder |
|---|---|---|---|
| occlusal section | % ash (LOI) | 60.9% | 60.6% |
|  | Vol. fraction in % | 41.4% v | 41.1% v |
|  | flexural strength | 892 MPa | 883 MPa |
|  | modulus of elasticity | 29094 MPa | 28762 MPa |
| middle section | ash | 56.5% | 44% |
|  | Vol. fraction in % | 36.7% v | 23.4% v |
|  | flexural strength | 757 MPa | 376 MPa |
|  | modulus of elasticity | 23887 MPa | 9153 MPa |
| gingival section | ash | 50.5% | 43.5% |
|  | Vol. fraction in % | 30.3% v | 22.9% v |
|  | flexural strength | 574 MPa | 361 MPa |
|  | modulus of elasticity | 16797 MPa | 8599 MPa |

What is claimed is:

1. A method for manufacturing a fiber-reinforced composite dental restoration selected from the group consisting of crowns, bridges, implanted prostheses, implant superstructures, inlay bridges, removable appliances, removable dentures, and structural components of dental restorations comprising the steps of
    (i) preparing a mould having a cavity;
    (ii) filling the cavity of the mould with a fiber-reinforced polymerizable material having a volume fraction of fibers comprising an organic matrix and a fiber component embedded within the organic matrix;
    (iii) pressing the fiber-reinforced polymerizable material in the mould using an elastic membrane; and
    (iv) curing the fiber-reinforced polymerizable material in the mould to form the finer-reinforced composite dental restoration;
    wherein the mould is designed in a way which allows excess organic matrix material to escape from the cavity during pressing thereby increasing the volume fraction of fibers in the fiber-reinforced polymerizable material.

2. A method according to claim 1, wherein the mould is provided with one or more drainages.

3. A method according to claim 1, wherein a pressure of about 2 bar is applied.

4. A method according to claim 1, wherein the polymerizable fiber-reinforced material is cured by light curing.

5. A method according to claim 1, wherein the cavity mould is overfilled.

6. A method according to claim 1 the mould is a silicone mould.

7. A method according to claim 1, wherein the mould is provided with one or more grooves connecting the inside of the cavity with the outside of the mould.

8. A method according to claim 7, wherein the grooves are 0.05 to 1.0 mm wide.

9. A method according to claim 1, wherein the cavity is provided with a void space able to take up excess matrix material.

10. A method according to claim 9, wherein the cavity is bevelled.

11. A method according to claim 1, wherein the fiber component comprises glass, ceramic nad/or silica fibers.

12. A method according to claim 11, wherein the fiber-reinforced polymerizable material comprises 45.0 to 65.0 % by weight of the fiber component.

13. A method according to claim 12, wherein the fiber-reinforced polymerizable material comprises 31.1 to 48.9 % by weight of the organic matrix material.

14. A method according to claim 11, wherein the organic materix comprises a methacrylate resin, dimethacrylate resin, dimethacrylate-based aromatic resin, epoxy-based aromatic resin, polymethacrylate resin and/or urethane methacrylate resin.

15. A method according to claim 15, wherein the organic matrix comprises a misture of Bis-GMA, decandiol dimethacrylate, truethylene-glycol dimethacrylate and urethane dimethacrylate.

16. A method according to claim 15, wherein the mixture comprises 24.5 to 38.6 % by weight Bis-GMA, 0.3 0.5 % by weight decandiol dimethacrylate, 6.2 9.7 % by weight triethleneglycol dimethacrylate and 0.1 % by weight urethane dimethacrylate.

17. A method according to claim 16, wherein a fiber-reinforced polymerizable material comprising 24.5 % by weight Bis-GMA, 0.3 % by weight decandiol dimethacrylaete, 6.2 % by weight triethylefelycol dimethacrylate, 0.1 % by weight urethane dimethacrylate, 3.5 % by weight dispersed silica, < 0.3 % by weight catalysts and stabilizers, < 0.1 % by weight pigments and 65.0 % by weight glass fibers is used.

18. A method for manufacturing a fiber-reinforced composite dental restoration with a narrow shoulder comprising the steps of
    (1) preparing a cast of a tooth which is to be restored;
    (2) applying a covering agent to partially cover the cast of the tooth and leaving only a tooth stump of the cast tooth uncovered;
    (3) placing a fiber-reinforced polymerizable material comprising an organic material matrix and a fiber component embedded onto the uncovered tooth stump of the cast of the tooth;
    (4) pressing the fiber-reinforced polymerizable material on the uncovered tooth stum of the cast of the tooth; and
    (5) curing the fiber-reinforced polymerizable material on the uncovered tooth stump of the cast of the tooth to form the fiber-reinforced composite dental restoration;
    wherein the covering agent is applied in a way such that a narrow shoulder which follows a line of a wall of the tooth to be restored and has steps having an edge length of 1 to 1.0 mm is formed on the fiber-reinforced composite dental restoration.

19. Method according to claim 18, whereina silicon covering agent is used.

* * * * *